United States Patent [19]
Wall et al.

[11] Patent Number: 6,040,313
[45] Date of Patent: Mar. 21, 2000

[54] WATER-SOLUBLE ESTERS OF CAMPTOTHECIN COMPOUNDS

[75] Inventors: Monroe E. Wall, Chapel Hill; Mansukh C. Wani, Durham, both of N.C.

[73] Assignee: Research Triangle Institute, Research Triangle Park, N.C.

[21] Appl. No.: 09/241,076

[22] Filed: Feb. 1, 1999

Related U.S. Application Data

[62] Division of application No. 08/818,725, Mar. 14, 1997, Pat. No. 5,916,896, which is a division of application No. 08/277,642, Jul. 20, 1994, Pat. No. 5,646,159.

[51] Int. Cl.$^7$ ................................................ A61K 31/44
[52] U.S. Cl. ............................................................ 514/283
[58] Field of Search ............................................. 514/283

[56] References Cited

U.S. PATENT DOCUMENTS

| | | |
|---|---|---|
| 4,031,098 | 6/1977 | Sugasawa et al. . |
| 4,473,692 | 9/1984 | Miyasaka et al. . |
| 4,545,880 | 10/1985 | Miyasaka et al. . |
| 4,604,463 | 8/1986 | Miyasaka et al. . |
| 4,914,205 | 4/1990 | Sawada et al. . |
| 4,943,579 | 7/1990 | Vishnuvajjala et al. . |
| 5,004,758 | 4/1991 | Boehm et al. . |
| 5,122,526 | 6/1992 | Wall et al. . |
| 5,122,606 | 6/1992 | Wani et al. . |
| 5,180,722 | 1/1993 | Wall et al. . |
| 5,225,404 | 7/1993 | Giovannella et al. . |
| 5,227,380 | 7/1993 | Wall et al. . |
| 5,244,903 | 9/1993 | Wall et al. . |
| 5,342,947 | 8/1994 | Lackey et al. . |
| 5,352,789 | 10/1994 | Hinz . |
| 5,401,747 | 3/1995 | Wall et al. . |
| 5,559,235 | 9/1996 | Luzzio . |
| 5,889,017 | 3/1999 | Giovanella et al. ................. 514/283 |

FOREIGN PATENT DOCUMENTS

| | | |
|---|---|---|
| 0 074 256 | 3/1983 | European Pat. Off. . |
| 0 220 601 | 5/1987 | European Pat. Off. . |
| 0 540 099 | 5/1993 | European Pat. Off. . |
| 59-5188 | 1/1984 | Japan . |
| 59-51287 | 3/1984 | Japan . |
| 59-51289 | 3/1984 | Japan . |
| 61-50985 | 3/1986 | Japan . |
| 61-85319 | 4/1986 | Japan . |
| 61-85389 | 4/1986 | Japan . |
| WO 95/10304 | 4/1995 | WIPO . |

OTHER PUBLICATIONS

Hertzberg et al, *Proc. Annu. Meet. Assoc. Cancer Res.*, 1989, AN 30:A2485 (Abstract).
Ohno et al, *Proc. Annu. Meet. Am. Soc. Clin. Oncol.*, 1989, AN 8:A1010 (Abstract).
Hertzberg et al, *J. Med. Chem.*, vol. 32, pp. 715–720, 1989 (Abstract).
Danishetsky et al, *J. Org. Chem.*, vol. 39, pp. 3430–3432 (1974).
Gilmour et al, *J. Mol. Cell. Biol.*, vol. 7, pp. 141–148 (1987).
Database WPI, Derwent Publications, Ltd., AN 89–179979/25, Dec. 1, 1987, EP 321 122.
Plattner et al, *J. Org. Chem.*, vol. 39, pp. 303–311 (1974).
Plattner et al, *J. Am, Chem. Soc.*, vol. 94, pp. 8613–8615 (1972).
Ronman et al, *J. of Lab. Com. and Radiopharm.*, vol. XVIII, pp. 319–329 (1979).
Nicholas et al, *J. Med. Chem.*, vol. 33, pp. 972–978 (1990).
Wani et al, *J. Med. Chem.*, vol. 23, pp. 554–560 (1980).
Wall et al, *J. Med. Chem.*, vol. 29, pp. 1553–1555 (1986).
Hsiang et al, *Cancer Research*, vol. 49, pp. 4385–4389 (1989).
Jaxel et al, *Cancer Research*, vol. 49, pp. 1465–1469 (1989).
Pommier et al, Proc. Annu. Meet. Am. Assoc. Cancer Res., AN 29:A1080 (1988).
Hsiang et al, Proc. Annu. Meet. Am. Assoc. Cancer Res., AN 30:A2476 (1989).
Hsiang et al, *J. Bio. Chem.*, vol. 260, pp. 14873–14878 (1985).
Wani et al, *J. Med. Chem.*, vol. 30, pp. 1774–1779 (1987).
Wani et al, *J. Med. chem.*, vol. 29, pp. 2358–2363 (1986).
Giovanella et al, *Science*, vol. 246, pp. 1046–1048 (1989).
Nagata et al, *Cancer Treatment Reports*, vol. 71, pp. 341–348 (1987).

*Primary Examiner*—Jerome D. Goldberg
*Attorney, Agent, or Firm*—Oblon, Spivak, McClelland, Maier & Neustadt, P.C.

[57] ABSTRACT

Non-toxic camptothecin prodrugs are prepared by esterifying the 20-position hydroxyl group of camptothecin derivatives.

5 Claims, No Drawings

WATER-SOLUBLE ESTERS OF CAMPTOTHECIN COMPOUNDS

This application is a Div of Ser. No. 08/818,725, filed on Mar. 14, 1997, now U.S. Pat. No. 5,916,896 which is a Div of Ser. No. 08/277,642, filed on Jul. 20, 1994, now U.S. Pat. No. 5,646,159.

BACKGROUND OF THE INVENTION

1. Field of the Invention

This invention relates to water-soluble camptothecin compounds. More particularly, the invention relates to esters of camptothecin compounds prepared by esterifying the hydroxyl group at the 20-position of camptothecin compounds to form nontoxic water-soluble prodrugs.

2. Discussion of the Background

Camptothecin is an optically active (20S) alkaloid isolated from the *Camptotheca acuminata* tree which is native to China. The naturally occurring compound and many derivatives thereof exhibit anti-tumor activity. Camptothecin is a fused ring system having the structure shown below.

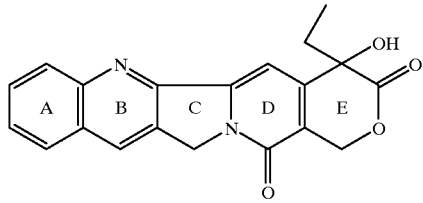

Major synthetic efforts have been directed to derivatizing the A-ring and/or the B-ring to improve cytotoxic activity and to improve water-solubility.

Camptothecin and camptothecin derivatives are cytotoxic compounds which can be used as chemotherapeutic agents. The cytotoxic activity of camptothecin compounds is believed to arise from the ability of these compounds to inhibit both DNA and RNA synthesis and to cause reversible fragmentation of DNA in mammalian cells. Camptothecin compounds inhibit the enzyme DNA topoisomerase I which is known to relax supercoiled DNA. This relaxation is brought about by breakage of one of the DNA strands in the formation of a covalent topoisomerase I-DNA complex. Camptothecin derivatives are believed to function by reversibly trapping the enzyme-DNA intermediate which is termed the "cleavable complex." Hsiang et al. (1989), Cancer Research, 49:4385–4389. The cleavable complex assay developed by Hsiang et al. is a standard test for determining the cytotoxic activity of camptothecin compounds.

Unfortunately, camptothecin and many camptothecin compounds are water insoluble. This water insolubility makes administration of camptothecin compounds difficult. Water soluble camptothecin derivatives have been prepared by derivatizing the A and B rings and by opening the lactone E-ring. See, for example, U.S. Pat. No. 4,981,968, U.S. Pat. No. 5,049,668 and EP 0 540,099. U.S. Pat. No. 4,914,205 discloses prodrug-type camptothecin compounds in which the lactone E-ring has been opened and modified to form an amide. U.S. Pat. No. 4,943,579 discloses camptothecin compounds in which the hydroxyl group at the 20-position is esterified to form camptothecin prodrugs which hydrolyze after injection to form the parent camptothecin compound.

A need continues to exist for new camptothecin compounds having high anti-tumor activity and yet low toxicity.

SUMMARY OF THE INVENTION

Accordingly, one object of this invention is to provide compounds which are non-toxic per se and after in vivo administration regenerate by hydrolysis, camptothecin compounds with high anti-tumor activity.

This and other objects which will become apparent from the following specification have been achieved by the discovery that esterifying the hydroxyl group at the 20-position forms non-toxic prodrugs which hydrolyze to the parent camptothecin compound.

DETAILED DESCRIPTION OF THE PREFERRED EMBODIMENTS

The present invention is based on the discovery that esterification of the hydroxyl group at the 20-position of camptothecin compounds produces a non-toxic water-soluble prodrug. The prodrug is non-toxic even though the parent camptothecin compound itself may be substantially more toxic. Hydrolysis of the ester formed at the 20-position reforms the parent camptothecin compound after administration thereby reducing the overall toxicity experienced by the patient during camptothecin therapy.

The toxicity or non-toxicity of the camptothecin esters of the present invention can be evaluated by monitoring weight loss in test animals such as mice which have been administered the ester compounds. By "non-toxic", as used herein with reference to the ester compounds of the present invention, is meant a compound which is not toxic according to Protocal 4, section 4.301(b)(3) where toxicity is defined as a weight loss of $\geq 4.0$ grams as reported in R. I. Geran, N. H. Greenberg, M. M. MacDonald, A. M. Schumacher and B. J. Abbott, Cancer Chemotherapy Reports, Part 3, Vol. 3, No. 2, September 1972.

U.S. Pat. No. 4,943,579 discloses the esterification of the hydroxyl group at the 20-position of camptothecin to form several prodrugs. This patent further discloses that the prodrugs are water soluble and are converted into the parent camptothecin compounds by hydrolysis. Surprisingly, it has now been discovered that prodrugs formed by esterifying the hydroxyl group at the 20-position are non-toxic in contrast to the toxicity of parent camptothecin compounds even though the esterified derivatives are hydrolyzed to the parent camptothecin compounds after administration. U.S. Pat. No. 4,943,579 does not suggest that prodrugs formed by esterifying the hydroxyl group at the 20-position are non-toxic relative to the parent compounds. The compounds disclosed by U.S. Pat. No. 4,943,579 are not within the scope of the present invention.

The compounds of the present invention are prepared by esterifying the 20-position hydroxyl group of a camptothecin compound to form an ester containing a water-soluble moiety. Generally, the camptothecin compound is initially suspended in methylene chloride or other inert solvent, stirred and cooled. To the cooled mixture is added one equivalent of an acid having the formula HOOC—CHR$^9$—NR$^{10}$R$^{11}$ or HOOC—(CH$_2$)$_m$—NR$^{10}$R$^{11}$, where m is an integer from 1–6, preferably 2–6, and R$^9$ is the side chain of one of the naturally occurring α-amino acids. R$^{10}$ and R$^{11}$ are, independently, hydrogen or C$_{1-8}$ alkyl. Suitable side chains R$^9$ are the side chains of the amino acids glycine, alanine, valine, leucine, isoleucine, phenylalanine, tyrosine, tryptophan, leucine, arginine, histidine, aspartate, glutamate, asparagine, glutamine, cysteine and methionine. Particularly preferred esters are glycinate esters. One equivalent of dicyclohexylcarbodiimide (DCC) and a catalytic amount of an amine base, preferably a secondary or tertiary amine, are also added to the mixture, which is then stirred to complete the reaction. Any precipitate which forms is removed by filtration and the product is isolated after removal of the solvent.

The free amine may be converted to an acid addition salt by the addition of a pharmaceutically acceptable acid. Suitable acids include both inorganic and organic acids. Suitable addition salts include, but are not limited to hydrochloride, sulfate, phosphate, diphosphate, hydrobromide, nitrate, acetate, malate, maleate, fumarate, tartrate, succinate, citrate, lactate, methanesulfonate, p-toluenesulfonate, palmoate, salicylate and stearate salts. The salts may be purified by crystallization from a suitable solvent.

Camptothecin and derivatives thereof have an asymmetric carbon atom at the 20-position and therefore exist in two enantiomeric forms, i.e. the (R) and (S) configurations. This invention includes both enantiomeric forms and all combinations of these forms, including racemic mixtures designated as (RS).

Any camptothecin compound having an available hydroxyl group may be used to prepare the ester compounds of the present invention. Suitable camptothecin compounds are described, for example, in U.S. Pat. No. 4,894,456, U.S. Pat. No. 4,981,968, U.S. Pat. No. 5,053,512, U.S. Pat. No. 5,049,668, U.S. Pat. No. 5,106,742, U.S. Pat. No. 5,180,722, U.S. Pat. No. 5,244,903, U.S. Pat. No. 5,227,380, U.S. Pat. No. 5,122,606, U.S. Pat. No. 5,122,526, U.S. Pat. No. 5,225,404, U.S. Pat. No. 4,914,205, U.S. Pat. No. 4,545,880, U.S. Pat. No. 4,604,463, U.S. Pat. No. 4,473,692, U.S. Pat. No. 4,031,098, EP 0 220 601, EP 0 074 256 and U.S. patent application Ser. Nos. 07/784,275 and 07/826,729 (EP 0 540 099). These U.S. applications and U.S. patents are incorporated herein by reference for a more complete description of camptothecin compounds which can be used to prepare the esters of the present invention.

Preferred hydroxyl group containing camptothecin compounds for use in the method of the present invention are camptothecin derivatives in which the A ring is substituted at the 9-, 10- or 9- and 10,11-positions. Suitable compounds have the structure shown below.

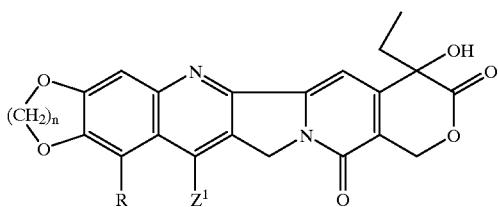

In the structure shown above, R is $NO_2$, $NH_2$, $N_3$, hydrogen, halogen (F, Cl, Br, I), COOH, OH, O—$C_{1-3}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$ alkyl)$_2$, O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2N(CH_2CH_2OH)_2$, O—, NH— and S—$CH_2CH_2CH_2N(CH_2CH_2CH_2OH_2)_2$, O—, NH— and S—$CH_2CH_2N(C_{1-3}$ alkyl)$_2$, O—, NH— and S—$CH_2CH_2CH_2N(C_{1-3}$ alkyl)$_2$, CHO or $C_{1-3}$ alkyl. Preferred compounds are those in which R is halogen, nitro or amino.

$Z^1$ in the structure shown above is H, $C_{1-8}$ alkyl, or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl, (6) $R^1$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl or $C_{1-6}$ alkoxy-$C_{1-6}$ alkyl and $R^2$ is —$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and -$COR^5$ where $R^5$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups. In the structure shown above, n is an integer of 1 or 2.

Preferred aryl groups are phenyl and naphthyl.

Other preferred hydroxyl group containing camptothecin compounds which can be used in the present invention have the structure shown below.

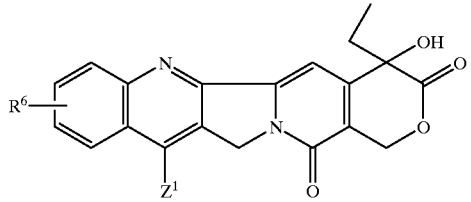

In this structure, $R^6$ is cyano, formyl, hydroxy, $C_{1-8}$ alkoxy, nitro, amino, halogen, trifluoromethyl, aminomethyl, azido, amido, hydrazino, $OC(O)R^7$ or $OC(O)$—$NR^7R^8$, where $R^7$ and $R^8$ are, independently, hydrogen or $C_{1-8}$ alkyl and $Z^1$ is as described above.

The preparation of these preferred compounds is described in U.S. Pat. No. 4,894,456, U.S. Pat. No. 5,180,722 and EP 0 540,099.

The E-ring of the camptothecin esters of the present invention has one of the structures shown below where m, $R^9$, $R^{10}$ and $R^{11}$ have the definitions given above.

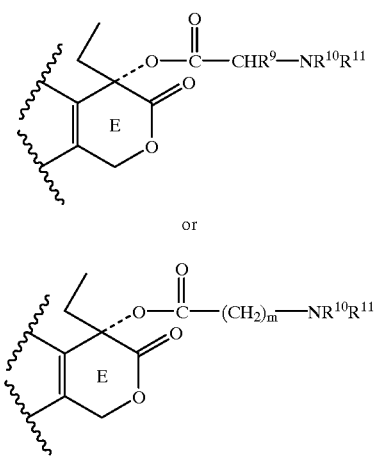

Hydrolysis of the exocyclic ester bond in vivo regenerates the parent hydroxyl group containing camptothecin compound.

The camptothecin prodrug compounds of the invention are administered in a dose which is effective to inhibit the enzyme topoisomerase I after in vivo hydrolysis. These effective amounts are generally from about 1–80 mg/kg of body weight per week, preferably about 2–40 mg/kg per week. The compounds of this invention may be administered in much higher doses than the corresponding parent compounds, because the prodrug compounds of the invention are substantially less toxic than the parent compounds. While not being bound by any particular scientific theory, it is believed that the lower toxicity of the present compounds is due to the esterification of the hydroxyl group at the 20-position of the camptothecin compound. It is thought that esterification of the hydroxyl group prevents hydrogen bonding between the hydrogen of the hydroxyl group and the carbonyl of the lactone E ring, where this hydrogen bonding is believed necessary for anti-leukemia and anti-tumor activity. In any event, the 20α-hydroxyl is required to be present in underivatized form for camptothecin and analogs to be active antileukemia and antitumor agents. Thus, CPT-20α-acetate is inactive, as is 20-desoxy-CPT. (Monroe E. Wall, Plant Antitumor Agents. V. Alkaloids with Antitumor Activity, Symposiumsberichtes, pp. 77–87, 4. Internationales Symposium, Biochemie and Physiologie der Alkaloide, Halle (Saale) 25, bis 28. June, 1969, edited by K. Mothes, K. Schreiber, and H. R. Schutte, Akademie-Verlag, Berlin, 1969.)

Slow hydrolysis of the ester group at the 20-position to yield the free hydroxyl group results in the slow controlled formation of the parent compound after administration of the ester prodrug. The slow formation of the parent compound is less toxic than administration of the corresponding amount of the parent compound initially. That is, the present invention allows one to administer a much larger dose of camptothecin compound as the prodrug than as the corresponding parent camptothecin compound. For example, 2–4 mg/kg 10,11-methylenedioxy-20(RS)-camptothecin administered ip has a toxic dose of 8.0 mg/kg as shown in Table II below. In contrast, the 20-glycinyl ester of this compound is non-toxic even when administered at 20 mg/kg. The present invention allows one to administer a 10 fold greater amount of the ester (which is hydrolyzed to the parent compound) than the parent compound itself. This property of the present compounds is surprisingly advantageous in reducing toxicity of the compounds during camptothecin therapy.

In addition, it is well-known that the lactone ring of CPT and analogs opens to a physiologically inactive open form at physiological pH, 7.2, (Thomas G. Burke, Awadesh K. Mishra, Mansukh C. Wani, and Monroe E. Wall, Lipid Bilayer Partitioning and Stability of Camptothecin Drugs, Biochem., 32(20), 5352 (1993)). The concentration of the lactone form in a body fluid, such as blood, is preserved because the lactone ring is prevented from hydrolyzing due to the presence of the 20-ester group in the compounds of the invention. This effect extends the lifetime of the active lactone compound in the animal after administration by preventing hydrolysis of the lactone ring.

The compounds of the present invention may be administered as a pharmaceutical composition containing the camptothecin compound and a pharmaceutically acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarally pure and non-toxic in the amounts used.

The water-soluble 20-hydroxyl esters of the present invention are substantially less toxic than the parent compounds from which the esters are prepared. The topoisomerase inhibitory activity of two camptothecin compounds, i.e., 9-amino-(20RS)-CPT and 10,11-MDO-(20RS)-CPT as well as the corresponding 20-glycinyl esters of these compounds is shown in Table I below.

TABLE I

| COMPOUND | $IC_{50}$ ($\mu M$) | S.E. |
| --- | --- | --- |
| 9-Amino-(20RS)-CPT | 0.44 | 0.12 |
| 9-Amino-20-glycinyl-(20RS)-CPT.HCl | 5.5 | 5.4 |
| 10,11-MDO-(20RS)-CPT | 0.067 | 0.038 |
| 10,11-MDO-20-glycinyl-(20RS)-CPT.HCl | 0.43 | 0.22 |

$IC_{50}$ = minimum drug concentration ($\mu M$) that inhibited the cleavable complex formation by 50%.
MDO = methylenedioxy
CPT = camptothecin
S.E. = standard error The results shown in Table I indicate that the parent compounds are considerably more active than the corresponding esters in inhibiting topoisomerase I as measured by the cleavable complex assay. In contrast to the parent compounds, the esters are much less toxic as shown in Table II below.

TABLE II

L-1210 Life Prolongation Assay[a]

| COMPOUND | dose regimen[b] | route | highest active dose, mg/kg (% T/C)[c] | active dose range, mg/kg | KE[d] | cures | toxic dose, mg/kg |
|---|---|---|---|---|---|---|---|
| 9-amino-20-glycinyl-(20RS)-CPT.HCl | Q04DX02[b] | ip | 10 (132) | 10 | −1.00 | 0 | NT* at 10 |
| 9-amino-20-glycinyl-(20RS)-CPT.HCl | Q04HX02 | iv | 5 (168) | 2.5–5.0 | 1.67 | 1/6 | NT at 5 |
| 10-amino-20-glycinyl-(20RS)-CPT.HCl | Q04HX02 | iv | 20 (225) | 1.25–20 | >5.97 | 0 | NT at 20 |
| 10,11-(methylenedioxy)-20-glycinyl-(20RS)-CPT.HCl | Q04HX02 | iv | 10 (236) | 1.25–20 | 5.97 | 3/6 | NT at 20 |
| 9-amino-(20S)-CPT | Q04DX02 | ip | 12 (250) | 5.3–12 | 4.8 | 1/6 | 10 |
| 10-amino-(20RS)-CPT | Q04DX02 | ip | 3.75 (365) | 1.35–3.74 | 5.97 | 3/6 | 6.25 |
| 10,11-(methylenedioxy)-(20RS)-CPT | Q04DX02 | ip | 2 (325) | 2–4 | 5.97 | 2/6 | 8.0 |

[a]Intraperitoneal transplants.
[b]Q04DX02 = ip injection on days 1 and 5. Q04HX02 = iv drug dosing on hours 1 and 5.
[c]% TC = (median survival time of treated/control animlas) × 100.
[d]log of initial tumor cell population minus log of tumor cell population at the end of treatment.
*NT = not toxic.

The ester compounds of the present invention are active in inhibiting topoisomerase I and yet are non-toxic over a wide active dose range as shown in Table II. The compounds of the present invention, therefore, enable one to administer greater amounts of the active camptothecin compound as its non-toxic ester prodrug while avoiding the toxicity of the parent compound. While not being bound to any particular theory, it is believed that the ester prodrug is slowly hydrolyzed to the parent camptothecin compound limiting damage to cellular tissues, in particular blood cells. The non-toxicity of the compounds of the present invention is an important improvement over prior art camptothecin compounds.

The ester compounds of the invention may be administered to treat leukemia and solid tumors in mammals, including humans. The esters of the present invention are prodrugs which are hydrolyzed to camptothecin compounds demonstrating inhibitory activity on topoisomerase I. The camptothecin compounds formed by hydrolysis of the esters of the invention are also effective in treating leukemia and solid tumors in mammals. Numerous camptothecin compounds have been shown to be effective against leukemia using the standard L1210 leukemia assay (Wall et al. (1993), Journal of Medicinal Chemistry, 36:2689–2700). High activity of camptothecin and camptothecin analogs has also been shown in the P388 leukemia assay (Wall (1983), Medical and Pediatric Oncology, 11:480A–489A). The later reference also provides a correlation between anti-leukemia activity as determined by the L1210 and the P388 leukemia assays with efficacy of camptothecin compounds against solid tumors. Compounds reported as active in the leukemia assays also have demonstrated activity in a number of solid tumors including a colon xenograft, a lung xenograft, a Walker sarcoma and a breast xenograft (Wall (1983), Table IV, page 484 A). Recent studies have confirmed the correlation between topoisomerase I inhibitory activity and anti-leukemia/anti-tumor activity of camptothecin compounds (Giovanella et al. (1989), Science, 246: 1046–1048). The compounds of the present invention are particularly effective in the treatment of colon, lung and breast solid tumors.

Other features of the invention will become apparent in the coarse of the following descriptions of exemplary embodiments which are given for illustration of the invention and are not intended to be limiting thereof.

EXAMPLES

Example 1

9-amino-20-O-glycinyl-(20RS)-CPT.HCl

A stirred clear yellow solution of 9-nitro-(20RS)-CPT (78.6 mg, 0.200 mmol), t-BOC-glycine (75 mg, 0.400 mmol) and 4-(N,N-dimethylamino)-pyridine (DMAP, 12 mg) in dimethyl formamide (DMF, 2 ml) was treated with DCC (84 mg, 0.400 mmol) at ambient temperature under a nitrogen atmosphere. Over the coarse of 1.5 hours, the reaction turned brown-green and hazy. The DMF was removed under high vacuum and the residue purified by chromatography with CHCl$_3$ as the eluting solvent. The crude product was isolated as a yellow solid and was re-crystallized from MeOH/CHCl$_3$ provide the nitro glycinyl ester as a pale yellow solid (62 mg).

The nitro compound was stirred with 10% Pd/C (12 mg) in absolute ethanol (12 ml) under one atmosphere H$_2$ for 1 hours. The mixture was then filtered to remove the catalyst and rinsed with MeOH/CHCl$_3$ (1:1, 3×5 ml). The filtrate was evaporated under reduced pressure to give the corresponding amine as a bright orange-yellow solid (18 mg). Recrystallization from methanol gave the pure compound (13 mg) as a pale orange-gold solid.

The t-BOC-protected ester was dissolved in methylene chloride (3 ml) and the resulting stirred bright yellow solution was treated dropwise with HCl-saturated dioxane (4 ml). Initial foaming subsided quickly, and after 1 hour the solvents were distilled under reduced pressure to give the title compound as a gray-brown solid. This material was dissolved in water (4 ml) and the resulting deep orange-yellow solution was filtered (0.45 μm membrane) and then lyophilized to provide a fluffy tan-brown solid (17 mg).

Example 2

10-amino-20-O-glycinyl-(20RS)-CPT.HCl

A stirred solution of 10-nitro-(20RS)-CPT (50 mg, 0.127 mmol) t-BOC-glycine (50 mg, 0.286 mmol) and DMAP (10 mg) in methylene chloride (1 ml) and DMF (10 ml) under a nitrogen atmosphere was treated at room temperature with DCC (70 mg, 0.340 mmol). Over 2 hours, the reaction became turbid and brown-green. The mixture was concentrated under reduced pressure, dissolved in CHCl$_3$ and purified by column chromatography (SiO$_2$, 10 g, CHCl$_3$). The nitro compound was isolated and re-crystallized from MeOH/CHCl$_3$ to provide a pale yellow solid.

The nitro compound (20 mg) was then dissolved in absolute ethanol (15 ml) by sonication. The hazy yellow solution was treated with one atmosphere hydrogen in the presence of 10% Pd/C for 1 hour. The resulting bright iridescent green mixture was filtered and the filter paper then washed with MeOH/CHCl$_3$. The evaporation of the solvent provided an orange-yellow solid (18 mg). Re-crystallization from MeOH/CHCl₃ gave the corresponding amino compound as a fine orange powder.

The amino compound was stirred in methylene chloride (8 ml), clarified by the addition of MeOH (1 ml), chilled to 0° C. and then treated over 3 minutes with HCl-saturated dioxane (4 ml). After warming to room temperature and standing for 2 hours, the solvent was evaporated under reduced pressure. The resulting orange solid was dissolved in water (3 ml) to give a bright orange solution. After filtration (0.45 µm membrane), the solution was frozen and lyophilized to afford the title compound as a fluffy orange solid (18 mg).

Example 3

10,11-MDO-20-O-glycinyl-(20RS)-CPT.HCl

To a stirred turbid mixture of 10,11-MDO-(20RS)-CPT (425 mg, 1.084 mmol) and dry methylene chloride (500 ml) was added t-BOC-glycine (475 mg, 2.714 mmol) and DMAP (125 mg). The mixture was chilled to 0° C., treated with DCC (600 mg, 2.913 mmol) and then left to warm to room temperature. After 20 hours, the reaction mixture was concentrated to 50 ml and filtered. After concentration to 20 ml and further filtration, the reaction mixture was purified by column chromatography (SiO₂, 40 g, CHCl₃). Evaporation of the solvent provided an off-white solid (185 mg). Re-crystallization from methanol/methylene chloride gave the amine ester as a white solid.

This ester (57 mg) was dissolved in stirred methylene chloride (15 ml) and the solution was cooled to 0° C. A solution of HCl-saturated dioxane (8 ml) was added dropwise over 3 minutes resulting in a turbid yellow solution. The mixture was warmed to room temperature, and after 1.5 hours the solvent was evaporated to give a crude product. This material was triturated with methylene chloride to remove unreacted amine ester. The remaining solid was dissolved in water (20 ml), the hazy blue-yellow solution was filtered (0.45 µm membrane), the translucent yellow-blue filtrate was frozen and lyophilized to provide the title compound as a bright yellow fluffy solid.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method of treating leukemia or solid tumors susceptible to CPT in a mammal in need thereof, comprising administering to said mammal an effective amount for treating said leukemia or said solid tumors susceptible to CPT, a camptothecin ester having the structure:

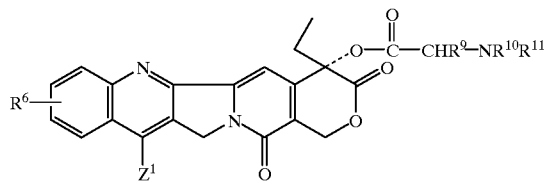

-continued

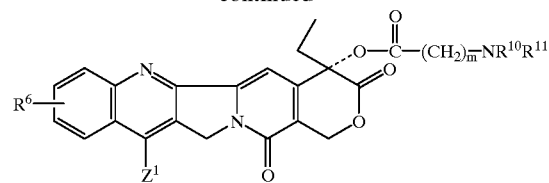

wherein $R^6$ is cyano, formyl, hydroxy, $C_{1-8}$ alkoxy, nitro, amino, halogen, trifluoromethyl, aminomethyl, azido, amido, hydrazino, $OC(O)R^7$ or $OC(O)NR^7R^8$ where $R^7$ and $R^8$ are, independently hydrogen or $C_{1-8}$ alkyl; and $Z^1$ is H, $C_{1-8}$ alkyl, $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl, (b) $R^1$ is hydrogen, $C_{1-6}$ alkyl, $C_{3-7}$ cycloalkyl, $C_{3-7}$ cycloalkyl-$C_{1-6}$ alkyl $C_{2-6}$ alkenyl, hydroxy-$C_{1-6}$ alkyl or $C_{1-6}$ alkoxy-$C_{1-6}$ alkyl and $R^2$ is —$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR^5$ where $R^5$ is hydrogen, $C_{1-6}$alkyl, perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

$R^9$ is the side chain of one or the naturally occurring α-amino acid selected from the group consisting of glycine, alanine, valine, leucine, isoleucine, serine, threonine, proline, phenylalanine, tyrosine, tryptophan, lysine, arginine, histidine, aspartate, glutamate, asparagine, glutamine, cysteine and methionine;

$R^{10}$ and $R^{11}$ are, independently, hydrogen or $C_{1-8}$ alkyl;

m is an integer of 1 to 6; and n is an integer of 1 or 2; and pharmaceutically acceptable salts thereof.

2. The method of claim 1, comprising administering 1–80 mg/kg body weight per week of camptothecin ester.

3. The method of claim 1, wherein said administering is oral or parenteral administering.

4. The method of claim 1, wherein said method is a method of treating colon, lung or brest solid tumor.

5. The method of claim 1, wherein said camptothecin ester is an ester of a compound selected from the group consisting of 9-chloro-20(S)-camptothecin, 9-amino-20(S)-camptothecin, 10-amino-20(S)-camptothecin and 10-chloro-20-(S)-camptothecin.

* * * * *